US012447346B2

(12) United States Patent
Annecchino et al.

(10) Patent No.: US 12,447,346 B2
(45) Date of Patent: Oct. 21, 2025

(54) SYSTEM AND METHOD FOR ADAPTIVE NEURAL STIMULATION

(71) Applicant: Boston Scientific Neuromodulation Corporation, Valencia, CA (US)

(72) Inventors: Luca A. Annecchino, London (GB); Que Doan, West Hills, CA (US); Rosana Esteller, Santa Clarita, CA (US); Matthew McDonald, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 394 days.

(21) Appl. No.: 18/153,862

(22) Filed: Jan. 12, 2023

(65) Prior Publication Data

US 2023/0226359 A1 Jul. 20, 2023

Related U.S. Application Data

(60) Provisional application No. 63/266,859, filed on Jan. 17, 2022.

(51) Int. Cl.
*A61N 1/36* (2006.01)

(52) U.S. Cl.
CPC ..... *A61N 1/36167* (2013.01); *A61N 1/36062* (2017.08); *A61N 1/36071* (2013.01)

(58) Field of Classification Search
CPC ............ A61N 1/36167; A61N 1/36062; A61N 1/36071
See application file for complete search history.

(56) References Cited

U.S. PATENT DOCUMENTS

| | | | |
|---|---|---|---|
| 6,181,969 | B1 | 1/2001 | Gord |
| 6,516,227 | B1 | 2/2003 | Meadows et al. |
| 8,606,362 | B2 | 12/2013 | He et al. |
| 8,620,436 | B2 | 12/2013 | Parramon et al. |
| 8,914,115 | B2 | 12/2014 | Giftakis et al. |
| 2013/0289665 | A1 | 10/2013 | Marnfeldt et al. |
| 2015/0080982 | A1 | 3/2015 | Funderburk |
| 2015/0157861 | A1 | 6/2015 | Aghassian |
| 2015/0231402 | A1 | 8/2015 | Aghassian |

(Continued)

FOREIGN PATENT DOCUMENTS

WO 2021/076234 A1 4/2021

OTHER PUBLICATIONS

International Search Report and Written Opinion regarding corresponding PCT Application No. PCT/US2023/060566, mailed Apr. 19, 2023.

*Primary Examiner* — Alyssa M Alter
(74) *Attorney, Agent, or Firm* — Lewis & Reese, PLLC

(57) ABSTRACT

Methods and systems for providing electrical stimulation to a patient's spinal cord using electrode leads implanted in the patient's spinal column are described. Embodiments involve cycling between durations during which stimulation is actively applied and durations when no stimulation is applied. The stimulation can be configured such that pain relief washes in during the active stimulation duration and continues for some part of the duration when no stimulation is being applied. Eventually the pain relief may wash out. The washout time may be modeled, so that stimulation may be resumed before the pain relief washes out. The stimulation may be below the patient's perception threshold.

16 Claims, 11 Drawing Sheets

(56) References Cited

U.S. PATENT DOCUMENTS

| | | | |
|---|---|---|---|
| 2015/0360038 | A1 | 12/2015 | Zottola et al. |
| 2018/0071520 | A1 | 3/2018 | Weerakoon et al. |
| 2018/0071527 | A1 | 3/2018 | Feldman et al. |
| 2018/0140831 | A1 | 5/2018 | Feldman et al. |
| 2019/0046800 | A1 | 2/2019 | Doan et al. |
| 2019/0083796 | A1 | 3/2019 | Weerakoon et al. |
| 2019/0262609 | A1 | 8/2019 | Brill et al. |
| 2019/0366104 | A1 | 12/2019 | Doan et al. |
| 2020/0009394 | A1* | 1/2020 | Huertas Fernandez ...................... A61N 1/025 |
| 2020/0147391 | A1 | 5/2020 | Moffitt et al. |
| 2020/0346019 | A1 | 11/2020 | Weiss et al. |
| 2021/0236829 | A1 | 8/2021 | Zhang et al. |
| 2021/0299448 | A1 | 9/2021 | Doan et al. |

* cited by examiner

SYSTEM AND METHOD FOR ADAPTIVE NEURAL STIMULATION

CROSS REFERENCE TO RELATED APPLICATIONS

This is a non-provisional of U.S. Provisional Patent Application Ser. No. 63/266,859, filed Jan. 17, 2022, to which priority is claimed, and which is incorporated herein by reference.

FIELD OF THE INVENTION

This application relates to Implantable Medical Devices (IMDs), generally, Spinal Cord Stimulators, more specifically, and to methods of control of such devices.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable neurostimulator device system.

An SCS system typically includes an Implantable Pulse Generator (IPG) 10 shown in FIG. 1. The IPG 10 includes a typically conductive biocompatible device case 12 that holds the IPG's circuitry and a battery 14 for providing power for the IPG to function. The IPG 10 is coupled to tissue-stimulating electrodes 16 via one or more electrode leads that form an electrode array 17. For example, one or more percutaneous leads 15 can be used having ring-shaped or split-ring electrodes 16 carried on a flexible body 18. In another example, a paddle lead 19 provides electrodes 16 positioned on one of its generally flat surfaces. Lead wires 20 within the leads are coupled to the electrodes 16 and to proximal contacts 21 insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12.

In the illustrated IPG 10, there are thirty-two electrodes (E1-E32), split between four percutaneous leads 15, or contained on a single paddle lead 19, and thus the header 23 may include a 2×2 array of eight-electrode lead connectors 22. However, the type and number of leads, and the number of electrodes, in an IPG is application specific and therefore can vary. The conductive case 12 can also comprise an electrode (Ec). In a SCS application, the electrode lead(s) are typically implanted in the spinal column proximate to the dura in a patient's spinal cord, preferably spanning left and right of the patient's spinal column. The proximal contacts 21 are tunneled through the patient's tissue to a distant location such as the buttocks where the IPG case 12 is implanted, at which point they are coupled to the lead connectors 22. In other IPG examples designed for implantation directly at a site requiring stimulation, the IPG can be lead-less, having electrodes 16 instead appearing on the body of the IPG 10 for contacting the patient's tissue. The IPG lead(s) can be integrated with and permanently connected to the IPG 10 in other solutions. The goal of SCS therapy is to provide electrical stimulation from the electrodes 16 to alleviate a patient's symptoms, such as chronic back pain.

IPG 10 can include an antenna 27*a* allowing it to communicate bi-directionally with a number of external devices used to program or monitor the IPG, such as a hand-held patient controller or a clinician's programmer described later with respect to FIG. 5. Antenna 27*a* as shown comprises a conductive coil within the case 12, although the coil antenna 27*a* can also appear in the header 23. When antenna 27*a* is configured as a coil, communication with external devices preferably occurs using near-field magnetic induction. IPG 10 may also include a Radio-Frequency (RF) antenna 27*b*. In FIG. 1, RF antenna 27*b* is shown within the header 23, but it may also be within the case 12. RF antenna 27*b* may comprise a patch, slot, or wire, and may operate as a monopole or dipole. RF antenna 27*b* preferably communicates using far-field electromagnetic waves, and may operate in accordance with any number of known RF communication standards, such as Bluetooth, Zigbee, MICS, and the like.

Stimulation in IPG 10 is typically provided by pulses, as shown in FIGS. 2A and 2B. Stimulation parameters typically include the amplitude of the pulses (A; whether current or voltage); the frequency (F) of the pulses; the pulse width (PW) of the pulses (or its individual phases as described below); the electrodes 16 (E) activated to provide such stimulation; and the polarity (P) of such active electrodes, i.e., whether active electrodes are to act as anodes that source current to the tissue or cathodes that sink current from the tissue. These and possibly other stimulation parameters taken together comprise a stimulation program that the IPG 10 can execute to provide stimulation to a patient.

The pulses in FIG. 2A comprise two pulse phases 30*a* and 30*b* each actively driven by stimulation circuitry 28 shown in FIG. 3. During the first phase 30*a*, electrode E4 has been selected as an anode and thus sources a positive current of amplitude +A to the tissue, while electrode E5 has been selected as a cathode and thus sinks a corresponding negative current of amplitude −A from the tissue. However, more than one electrode may act as an anode at a given time, and more than one electrode may act as a cathode at a given time. Stimulation may also occur using the case electrode Ec, as shown in FIG. 3.

The pulses as shown in FIG. 2A, with two actively-driven phases 30*a* and 30*b*, are typically known as "biphasic" pulses, with phases 30*a* and 30*b* having opposite polarity. (A short interphase period may intervene between the two phases 30*a* and 30*b* during which no current flows, as described below, although this isn't shown). The use of biphasic pulses are useful in charge recovery, which can be necessary in light of capacitances in the current path established between the selected electrodes, as explained further below. Although not shown, each of the phases 30*a* and 30*b* could be broken up into a series of higher-frequency pulses, which is often referred to as a "burst" of pulses, as is well known.

The stimulation circuitry 28 as shown in FIG. 3 includes one or more current source circuits $\mathbf{40}_i$ and one or more current sink circuits $\mathbf{42}_i$. The sources and sinks $\mathbf{40}_i$ and $\mathbf{42}_i$ can comprise Digital-to-Analog converters (DACs), and may be referred to as PDACs $40_i$ and NDACs $42_i$ in accordance with the Positive (sourced, anodic) and Negative (sunk, cathodic) currents they respectively issue. In the example shown, a NDAC/PDAC $40_i/42_i$ pair is dedicated (hardwired) to a particular electrode node ei 39. Each electrode node ei 39 is connected to an electrode Ei 16 via a DC-blocking capacitor Ci 38, for the reasons explained below. The stimulation circuitry 28 in this example also supports selection of the conductive case 12 as an electrode (Ec 12), which case electrode is typically selected for monopolar stimulation. PDACs $40_i$ and NDACs $42_i$ can also comprise voltage sources. Although not shown, switching matrices can intervene between the one or more PDACs $40_i$ and the electrode nodes ei 39, and between the one or more NDACs $42_i$ and the electrode nodes. Switching matrices allows one or more of the PDACs or one or more of the NDACs to be connected to one or more anode or cathode electrode nodes at a given time.

The stimulation circuitry 28 is configured by the stimulation parameters, which may be provided to the stimulation circuitry 28 by controller circuitry 29 in the IPG 10. Controller circuitry 29 may comprise a microcontroller, microprocessor, microcomputer, an FPGA, other digital logic structures, etc., which is capable of executing instructions an electronic device. Controller circuitry 29 may comprise a separate component, or may be integrated with an Application Specific Integrated Circuit (ASIC) that includes the stimulation circuitry 28 as well as other circuitry necessary to operate various function of the IPG 10. Proper control of the PDACs $40_i$ and NDACs $42_i$ via the stimulation parameters allows any of the electrodes 16 to act as anodes or cathodes to create a current A of the prescribed amplitude A through a patient's tissue, R, hopefully with good therapeutic effect. In the example shown, and during the first phase 30*a* in which electrodes E4 and E5 are selected as an anode and cathode respectively, PDAC $40_4$ and NDAC $42_5$ are activated and digitally programmed to produce the desired current, A, with the correct timing (e.g., in accordance with the prescribed frequency F and pulse width PWa). During the second phase 30*b* (PWb), PDAC $40_5$ and NDAC $42_4$ would be activated to reverse the polarity of the current. More than one anode electrode and more than one cathode electrode may be selected at one time, and thus current can flow through the tissue R between two or more of the electrodes 16. Power for the stimulation circuitry 28 is provided by a compliance voltage VH, as described in further detail in U.S. Patent Application Publication 2013/0289665. Other examples of stimulation circuitries and details of various PDAC and NDAC circuits are disclosed in U.S. Pat. Nos. 6,181,969, 8,606,362, 8,620,436, U.S. Patent Application Publications 2018/0071520 and 2019/0083796. Note that the stimulation circuitry 28 is capable of independently setting the current at any of the electrodes-what is sometimes known as a Multiple Independent Current Control (MICC).

A DC-blocking capacitor Ci 38 is placed in series between each of the electrode nodes ei 39 and the electrodes Ei 16 (including the case electrode Ec 12). The DC-blocking capacitors 38 act as a safety measure to prevent DC current injection into the patient, as could occur for example if there is a circuit fault in the stimulation circuitry 28. The DC-blocking capacitors 38 are typically provided off-chip (off of the ASIC(s)), and instead may be provided in or on a circuit board in the IPG 10 used to integrate its various components, as explained in U.S. Patent Application Publication 2015/0157861.

As noted above, biphasic pulses as shown in FIG. 2A can be useful to recover charge stored on capacitances in the current path and in particular on the DC-blocking capacitors 38. When constant current A is driven during the first phase 30*a*, the capacitors in the current path (C4 and C5) will store charge at a rate dV/dt=I/C, and thus building a voltage across these capacitors (Vc4 and Vc5). When the polarity of this current is reversed during the second phase 30*b*, this stored charge is recovered, and the voltage across the capacitors preferably returns to zero before the issuance of the next pulse (i.e., before the next phase 30*a*). Using biphasic pulses in this manner is sometimes referred to as "active" charge recovery, because the charge stored during the first phase 30*a* is recovered by a current actively driven by the stimulation circuitry 28 during the second phase 30*b*. It is usually preferred during active charge recovery that the phases 30*a* and 30*b* are charge balanced—that is, that the amount of charge passed during the first phase 30*a* equal the amount of charge passed during the second phase 30*b*. This can be achieved by setting the current amplitude and the pulse widths to equal values during both phases (|+A|=|−A|; PWa=PWb). However, this is not strictly necessary, and charge balancing can also be achieved if the product of the amplitude and pulse width is equal for both phases (or more generally if the area under their curves is equal).

Stimulation pulses may also be provided using monophasic pulses followed by the use of passive charge recovery, as shown in FIG. 2B. Such monophasic pulses comprise only a single active phase 30*a*, which is actively driven as before. Because this phase 30*a* will charge capacitances in the current path as just described, it is again prudent to recover such charge, but this occurs passively without the stimulation circuitry 28 (i.e., the PDACs and NDACs) driving an active current. Specifically, passive charge recovery switches $41_i$ are provided in the stimulation circuitry 28 (FIG. 3). A switch $41_i$ is coupled between each of the electrode nodes ei 39 and a reference potential. In the depicted example, this reference potential comprises the voltage of the battery 14 (Vbat), although another reference potential can be used. After the first pulse phase 30*a* is issued, one or more of these switches $41_i$ (all, or at least $41_4$ and $41_5$ whose electrodes nodes e4 and e5 were involved in providing the current during the first phase) are closed during a passive charge recovery period 30*c* (FIG. 2B). This places the capacitors charged during the first phase in parallel between the reference potential (Vbat), and the patient's tissue, R. As a result, and as shown in FIG. 2B, a current pulse of opposite polarity will flow at each electrode as the capacitors discharge, which current will exponentially decay at a rate depending of the values of the capacitances and the resistances inherent in the IPG's circuitry and the tissue R. Preferably, switches $41_i$ are closed during period 30*c* for a duration sufficient to effectively recover all charge that was stored on capacitive elements (e.g., capacitors 38) during the first phase 30*a*. At the end of passive charge recovery period, the switches 41; can again be opened. Passive charge recovery is more fully explained in U.S. Patent Application Publications 2018/0071527 and 2018/0140831.

Note that passive charge recovery can also be used with the biphasic pulses shown in FIG. 2A. Thus, a passive charge recovery period 30*c* may follow the second actively-driven phase 30*b*. Even if the actively-driven phases 30*a* and 30*b* are designed to be charge balanced, non-idealities may not result in perfect charge balancing, and so providing passive charge recovery during phase 30*c* can be prudent to assure that charge is fully recovered before the issuance of a next pulse. Examples of active, passive, and combined active-passive charge recovery are discussed in more detail below.

FIG. 4 shows an external trial stimulation environment that may precede implantation of an IPG 10 in a patient. During external trial stimulation, stimulation can be tried on a prospective implant patient without going so far as to implant the IPG 10. Instead, a trial electrode array 17' comprising one or more leads (e.g., one or more percutaneous leads 15 or paddle leads 19) are implanted in the patient's tissue 32 at a target location 34, such as within the spinal column as explained earlier. The proximal ends of the leads of the trial electrode array 17' exit an incision 36 and are connected to an External Trial Stimulator (ETS) 40. The ETS 40 generally mimics operation of the IPG 10, and thus can provide stimulation pulses to the patient's tissue as explained above. See, e.g., U.S. Pat. No. 9,259,574, disclosing a design for an ETS. The ETS 40 is generally worn externally by the patient for a short while (e.g., two weeks), which allows the patient and his clinician to experiment with different stimulation parameters to try and find a stimulation program that alleviates the patient's symptoms (e.g., pain). If external trial stimulation proves successful, the trial electrode array 17' is explanted, and a full IPG 10 and electrode array 17 are implanted as described above; if unsuccessful, the trial electrode array 17' is simply explanted.

Like the IPG 10, the ETS 40 can include one or more antennas to enable bi-directional communications with external devices, explained further with respect to FIG. 5. Such antennas can include a near-field magnetic-induction coil antenna **42*a*, and/or a far-field RF antenna 42*b*, as described earlier. ETS 40 may also include stimulation circuitry able to form the stimulation pulses in accordance with a stimulation program, which circuitry may be similar or identical to the stimulation circuitry 28 present in the IPG 10. ETS 40** may also include a battery (not shown) for operational power.

FIG. 5 shows various external devices that can wirelessly communicate data with the IPG 10 and the ETS 40, including a patient hand-held external remote controller (RC) 45, and a clinician programmer (CP) 50. Both of devices 45 and 50 can be used to send a stimulation program to the IPG 10 or ETS 40—that is, to program their stimulation circuitries to produce pulses with a desired shape and timing described earlier. Both devices 45 and 50 may also be used to adjust one or more stimulation parameters of a stimulation program that the IPG 10 or ETS 40 is currently executing. Devices 45 and 50 may also receive information from the IPG 10 or ETS 40, such as various status information, etc.

The RC 45 can be as described in U.S. Patent Application Publication 2015/0080982 for example, and may comprise a dedicated controller configured to work with the IPG 10. RC 45 may also comprise a general purpose mobile electronics device such as a mobile phone which has been programmed with a Medical Device Application (MDA) allowing it to work as a wireless controller for the IPG 10 or ETS 40, as described in U.S. Patent Application Publication 2015/0231402. RC 45 includes a user interface, including means for entering commands (e.g., buttons or icons) and a display 46. The RC 45's user interface enables a patient to adjust stimulation parameters, although it may have limited functionality when compared to the more-powerful clinician programmer 50, described shortly.

The RC 45 can have one or more antennas capable of communicating with the IPG 10 and ETS 40. For example, the RC 45 can have a near-field magnetic-induction coil antenna **47*a* capable of wirelessly communicating with the coil antenna 27*a* or 42*a* in the IPG 10 or ETS 40. The RC 45 can also have a far-field RF antenna 47*b* capable of wirelessly communicating with the RF antenna 27*b* or 42*b* in the IPG 10 or ETS 40. The RC 45 can also have controller circuitry 48 such as a microprocessor, microcomputer, an FPGA, other digital logic structures, etc., which is capable of executing instructions an electronic device. Controller circuitry 48 can for example receive patient adjustments to stimulation parameters, and create a stimulation program to be wirelessly transmitted to the IPG 10 or ETS 40**.

Clinician programmer 50 is described further in U.S. Patent Application Publication 2015/0360038, and is only briefly explained here. The clinician programmer 50 can comprise a computing device 51, such as a desktop, laptop, or notebook computer, a tablet, a mobile smart phone, a Personal Data Assistant (PDA)-type mobile computing device, etc. In FIG. 5, computing device 51 is shown as a laptop computer that includes typical computer user interface means such as a screen 52, a mouse, a keyboard, speakers, a stylus, a printer, etc., not all of which are shown for convenience. Also shown in FIG. 5 are accessory devices for the clinician programmer 50 that are usually specific to its operation as a stimulation controller, such as a communication "wand" 54, and a joystick 58, which are coupleable to suitable ports on the computing device 51, such as USB ports 59 for example.

The antenna used in the clinician programmer 50 to communicate with the IPG 10 or ETS 40 can depend on the type of antennas included in those devices. If the patient's IPG 10 or ETS 40 includes a coil antenna **27*a* or 42*a*, wand 54 can likewise include a coil antenna 56*a* to establish near-filed magnetic-induction communications at small distances. In this instance, the wand 54 may be affixed in close proximity to the patient, such as by placing the wand 54 in a belt or holster wearable by the patient and proximate to the patient's IPG 10 or ETS 40. If the IPG 10 or ETS 40 includes an RF antenna 27*b* or 42*b*, the wand 54, the computing device 51, or both, can likewise include an RF antenna 56*b* to establish communication with the IPG 10 or ETS 40 at larger distances. (Wand 54 may not be necessary in this circumstance). The clinician programmer 50** can also establish communication with other devices and networks, such as the Internet, either wirelessly or via a wired link provided at an Ethernet or network port.

To program stimulation programs or stimulation parameters for the IPG 10 or ETS 40, the clinician interfaces with a clinician programmer graphical user interface (GUI) 64 provided on the display 52 of the computing device 51. As one skilled in the art understands, the GUI 64 can be rendered by execution of clinician programmer software 66 on the computing device 51, which software may be stored in the device's non-volatile memory 68. One skilled in the art will additionally recognize that execution of the clinician programmer software 66 in the computing device 51 can be facilitated by control circuitry 70 such as a microprocessor, microcomputer, an FPGA, other digital logic structures, etc., which is capable of executing programs in a computing device. Such control circuitry 70, in addition to executing the clinician programmer software 66 and rendering the GUI 64, can also enable communications via antennas **56*a* or 56*b* to communicate stimulation parameters chosen through the GUI 64 to the patient's IPG 10**.

A portion of the GUI 64 is shown in one example in FIG. 6. One skilled in the art will understand that the particulars of the GUI 64 will depend on where clinician programmer software 66 is in its execution, which may depend on previous GUI selections the clinician has made. FIG. 6 shows the GUI 64 at a point allowing for the setting of stimulation parameters for the patient's IPG 10 or ETS 40. While GUI 64 is shown as operating in the clinician programmer 50, the user interface of the external controller 45 may provide similar functionality.

Shown to the right are interfaces where specific stimulation parameters can be defined for a stimulation program. Values for stimulation parameters relating to the shape of the waveform (A; in this example, current; PW; F) are shown in a waveform parameter interface 84, including buttons the clinician can use to increase or decrease these values. Stimulation parameters relating to the electrodes 16 (the active electrodes and their polarities), are made adjustable in an electrode parameter interface 86. Electrode parameters are also visible and can be manipulated in a leads interface 92 that displays the electrode array 17 (or 17') in generally their proper position with respect to each other, for example, on the left and right sides of the spinal column (only two leads are shown for simplicity). A cursor 94 (or other selection means such as a mouse pointer) can be used to select a particular electrode in the leads interface 92. Buttons in the electrode parameter interface 86 allow the selected electrode (including the case electrode, Ec) to be designated as an anode, a cathode, or off. The electrode parameter interface 86 further allows the relative strength of anodic or cathodic current of the selected electrode to be specified in terms of a percentage, X. This is particularly useful if more than one electrode is to act as an anode or cathode at a given time, as explained in the '038 Publication. In accordance with the example waveforms shown in FIGS. 2A and 2B, as shown in the leads interface 92, electrode E4 has been selected as the only anode to source current, and this electrode receives X=100% of the specified anodic current, +A. Likewise, electrode E5 has been selected as the only cathode to sink current, and this electrode receives X=100% of that cathodic current, −A. Again, more than one electrode can be selected to act as an anode or cathode at one time, with those electrodes sharing the anodic current +A or cathodic current −A. For example, electrodes E3 and E4 can both be selected to act as anode electrodes, with E3 receiving 30% of +A, and E4 receiving 70% of +A. GUI 64 can include other advanced options not shown as well, which for example allow for setting of a duty cycle (on/off time) for the stimulation pulses, setting a ramp-up time over which stimulation pulses will reach its programmed amplitude (A), options to specify the use of biphasic waveforms and/or passive charge recovery, etc.

SUMMARY

Disclosed herein is a method of providing electrical stimulation to a patient's spinal cord to treat pain in the patient using one or more electrode leads implantable in the patient's spinal column, wherein each electrode lead comprises a plurality of electrodes, the method comprising: providing a model associating first durations during which stimulation comprising a plurality of stimulation pulses is to be issued with second durations during which no stimulation is to be issued, using the model to select a first duration and an associated second duration, and using one or more of the electrodes to provide the electrical stimulation to the patient according to the selected first and second durations. According to some embodiments, the electrical stimulation is configured to be below the patient's perception threshold and to provide pain relief to the patient. According to some embodiments, the electrical stimulation is configured so that the pain relief washes in in a period of one hour or less. According to some embodiments, the electrical stimulation is configured so that the pain relief washes in in a period of ten seconds or less. According to some embodiments, the electrical stimulation is configured so that the pain relief does not wash out faster than the second duration. According to some embodiments, the model uses one or more stimulation parameters to select the first and second durations. According to some embodiments, the one or more parameters comprise one or more of stimulation intensity, stimulation amplitude, and/or stimulation dose. According to some embodiments, the one or more parameters comprise parameters determined using one or more sensors selected from the group consisting of accelerometers, motion detectors, heart rate monitors, sleep sensors. According to some embodiments, the one or more parameters comprise parameters determined from electrical signals recorded at one or more of the electrodes. According to some embodiments, the method further comprises deriving the model. According to some embodiments, deriving the model comprises: (a) providing test stimulation to the patient for a test first duration, (b) turning off the test stimulation at the end of the test first duration, (c) after a test second duration following the turning off the test stimulation, receiving an indication that the patient has turned on the stimulation, (d) increasing the length of the test first duration, (e) repeating steps (a)-(d) a plurality of times to collect a plurality test first durations and test second durations, and (f) modeling a relationship between test first durations and test second durations.

Also disclosed herein is a system for providing electrical stimulation to a patient's spinal cord to treat pain in the patient using one or more electrode leads implantable in the patient's spinal column, wherein each electrode lead comprises a plurality of electrodes, the system comprising: a memory programmed with a model associating first durations during which stimulation comprising a plurality of stimulation pulses is to be issued with second durations during which no stimulation is to be issued, and control circuitry configured to use the model to select a first duration and an associated second duration, and to cause stimulation circuitry to provide the electrical stimulation to the patient using one or more of the electrodes according to the selected first and second durations. According to some embodiments, the electrical stimulation is configured to be below the patient's perception threshold and to provide pain relief to the patient. According to some embodiments, the electrical stimulation is configured so that the pain relief washes in in a period of one hour or less. According to some embodiments, the electrical stimulation is configured so that the pain relief washes in in a period of ten seconds or less. According to some embodiments, the electrical stimulation is configured so that the pain relief does not wash out faster than the second duration. According to some embodiments, the model uses one or more stimulation parameters to select the first and second durations. According to some embodiments, the one or more stimulation parameters comprise one or more of stimulation intensity, stimulation amplitude, and/or stimulation dose. According to some embodiments, the one or more stimulation parameters comprise parameters determined using one or more sensors selected from the group consisting of accelerometers, motion detectors, heart rate monitors, sleep sensors. According to some embodiments, the one or more stimulation parameters comprise parameters determined from electrical signals recorded at one or more of the electrodes. According to some embodiments, the control circuitry is further configured to derive the model. According to some embodiments, deriving the model comprises: (a) providing test stimulation to the patient for a test first duration, (b) turning off the test stimulation at the end of the test first duration, (c) after a test second duration following the turning off the test stimulation, receiving an indication that the patient has turned on the stimulation, (d) increasing the length of the test first duration, (e) repeating steps (a)-(d) a plurality of times to collect a plurality test first durations and test second durations, and (f) modeling a relationship between test first durations and test second durations.

Also disclosed herein is a method of providing electrical stimulation to a patient's spinal cord to treat pain in the patient using one or more electrode leads implantable in the patient's spinal column, wherein each electrode lead comprises a plurality of electrodes, the method comprising: determining a first duration during which electrical stimulation is to be provided to the patient, using the first duration to determine a second duration during which no stimulation is to be provided, using one or more of the electrodes to provide the electrical stimulation comprising a plurality of pulses to the patient during the first duration, ceasing stimulation at the end of the first duration, and automatically resuming stimulation at the end of the second duration. According to some embodiments, the second duration is configured to be shorter than a washout time for pain relief provided by the electrical stimulation during the first duration. According to some embodiments, the electrical stimulation is configured to be below the patient's perception threshold and to provide pain relief to the patient. According to some embodiments, the electrical stimulation is configured so that the pain relief washes in in a period of one hour or less. According to some embodiments, the electrical stimulation is configured so that the pain relief washes in in a period of ten seconds or less. According to some embodiments, the method comprises using one or more stimulation parameters to determine the first and second durations. According to some embodiments, the one or more parameters comprise one or more of stimulation intensity, stimulation amplitude, and/or stimulation dose. According to some embodiments, the one or more parameters comprise parameters determined using one or more sensors selected from the group consisting of accelerometers, motion detectors, heart rate monitors, sleep sensors. According to some embodiments, the one or more parameters comprise parameters determined from electrical signals recorded at one or more of the electrodes.

Also disclosed herein is a system for providing electrical stimulation to a patient's spinal cord to treat pain in the patient using one or more electrode leads implantable in the patient's spinal column, wherein each electrode lead comprises a plurality of electrodes, the system comprising: control circuitry configured to: determine a first duration during which electrical stimulation is to be provided to the patient, use the first duration to determine a second duration during which no stimulation is to be provided, use one or more of the electrodes to provide the electrical stimulation comprising a plurality of pulses to the patient during the first duration, cease stimulation at the end of the first duration, and automatically resume stimulation at the end of the second duration. According to some embodiments, the second duration is configured to be shorter than a washout time for pain relief provided by the electrical stimulation during the first duration. According to some embodiments, the electrical stimulation is configured to be below the patient's perception threshold and to provide pain relief to the patient. According to some embodiments, the electrical stimulation is configured so that the pain relief washes in in a period of one hour or less. According to some embodiments, the electrical stimulation is configured so that the pain relief washes in in a period of ten seconds or less. According to some embodiments, one or more stimulation parameters are used to determine the first and second durations. According to some embodiments, the one or more parameters comprise one or more of stimulation intensity, stimulation amplitude, and/or stimulation dose. According to some embodiments, the one or more parameters comprise parameters determined using one or more sensors selected from the group consisting of accelerometers, motion detectors, heart rate monitors, sleep sensors. According to some embodiments, the one or more parameters comprise parameters determined from electrical signals recorded at one or more of the electrodes. According to some embodiments, the control circuitry is control circuitry of an implantable pulse generator (IPG). According to some embodiments, the control circuitry is control circuitry of and external controller for an implantable pulse generator (IPG).

Also disclosed herein is a method of providing electrical stimulation to a patient's spinal cord to treat pain in the patient using one or more electrode leads implantable in the patient's spinal column, wherein each electrode lead comprises a plurality of electrodes, the method comprising: (a) providing test stimulation to the patient for a test first duration, (b) turning off the test stimulation at the end of the test first duration, (c) after a test second duration following the turning off the test stimulation, receiving an indication that the patient has turned on the stimulation, (d) increasing the length of the test first duration, (e) repeating steps (a)-(d) a plurality of times to collect a plurality test first durations and test second durations, and (f) modeling a relationship between test first durations and test second durations. According to some embodiments, the modeled relationship between the test first durations and the test second durations indicates a washout time for pain relief provided by the electrical stimulation as a function of a stimulation duration.

Also disclosed herein is a system for providing electrical stimulation to a patient's spinal cord to treat pain in the patient using one or more electrode leads implantable in the patient's spinal column, wherein each electrode lead comprises a plurality of electrodes, the system comprising: control circuitry configured to: (a) provide test stimulation to the patient for a test first duration, (b) turn off the test stimulation at the end of the test first duration, (c) after a test second duration following the turning off the test stimulation, receive an indication that the patient has turned on the stimulation, (d) increase the length of the test first duration, (e) repeat steps (a)-(d) a plurality of times to collect a plurality test first durations and test second durations, and (f) model a relationship between test first durations and test second durations. According to some embodiments, the modeled relationship between the test first durations and the test second durations indicates a washout time for pain relief provided by the electrical stimulation as a function of a stimulation duration. According to some embodiments, the control circuitry is control circuitry of an implantable pulse generator (IPG). According to some embodiments, the control circuitry is control circuitry of and external controller for an implantable pulse generator (IPG).

The invention may also reside in the form of a programed external device (via its control circuitry) for carrying out the above methods, a programmed IPG or ETS (via its control circuitry) for carrying out the above method, a system including a programmed external device and IPG or ETS for carrying out the above methods, or as a computer readable media for carrying out the above methods stored in an external device or IPG or ETS.

DETAILED DESCRIPTION

Figure 1:
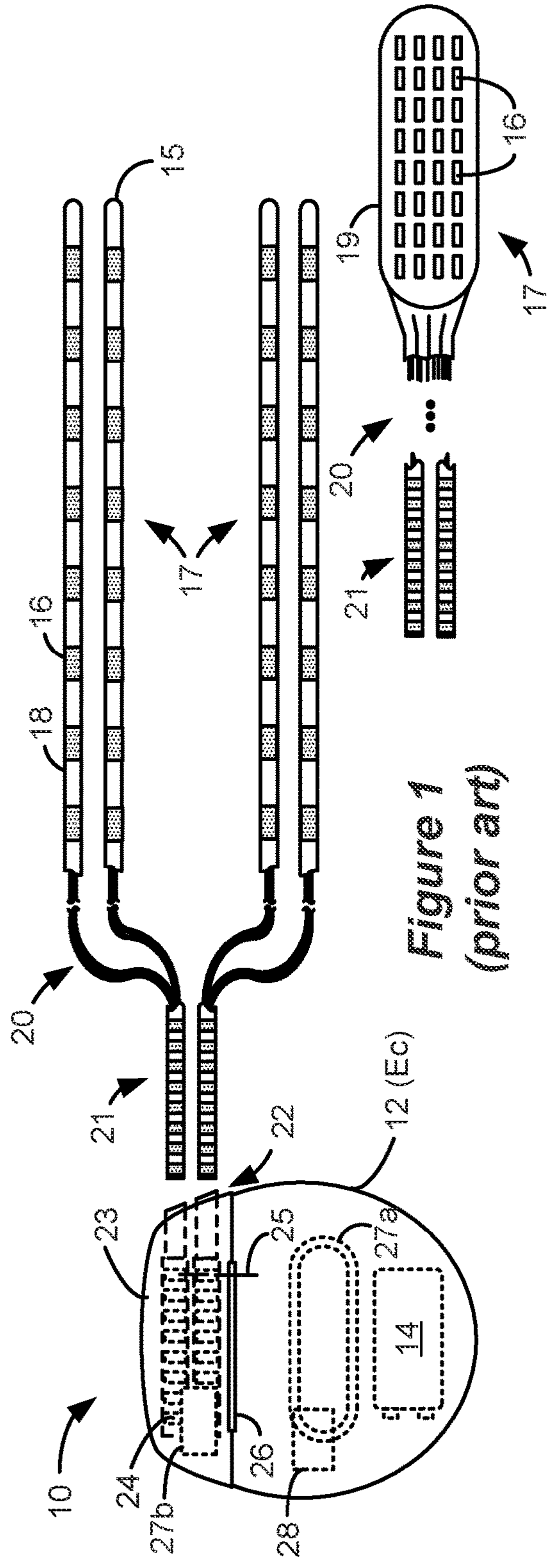
Figure 1 (prior art)
FIG. 1 shows an Implantable Pulse Generator (IPG) useable for Spinal Cord Stimulation (SCS), in accordance with the prior art.
Figure 2A:
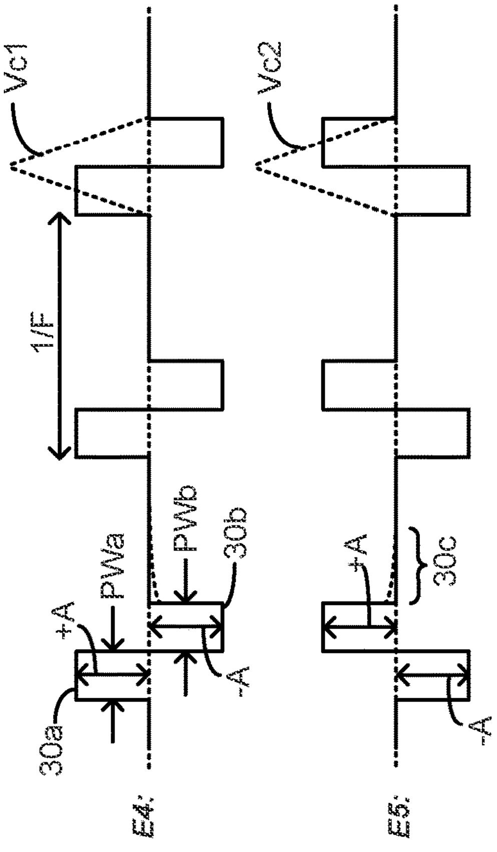
Figure 2A (prior art)
FIGS. 2A and 2B show examples of stimulation pulses producible by the IPG employing active charge recovery and passive charge recovery respectively, in accordance with the prior art.
Figure 2B:
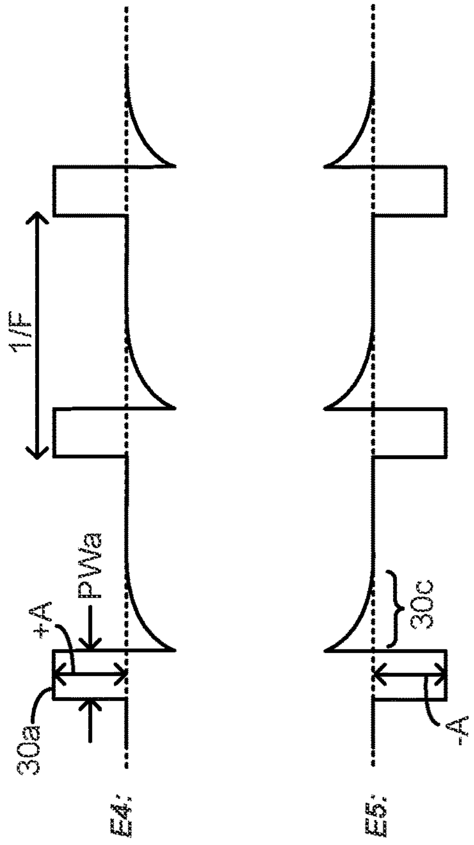
Figure 2B (prior art)
Figure 3:
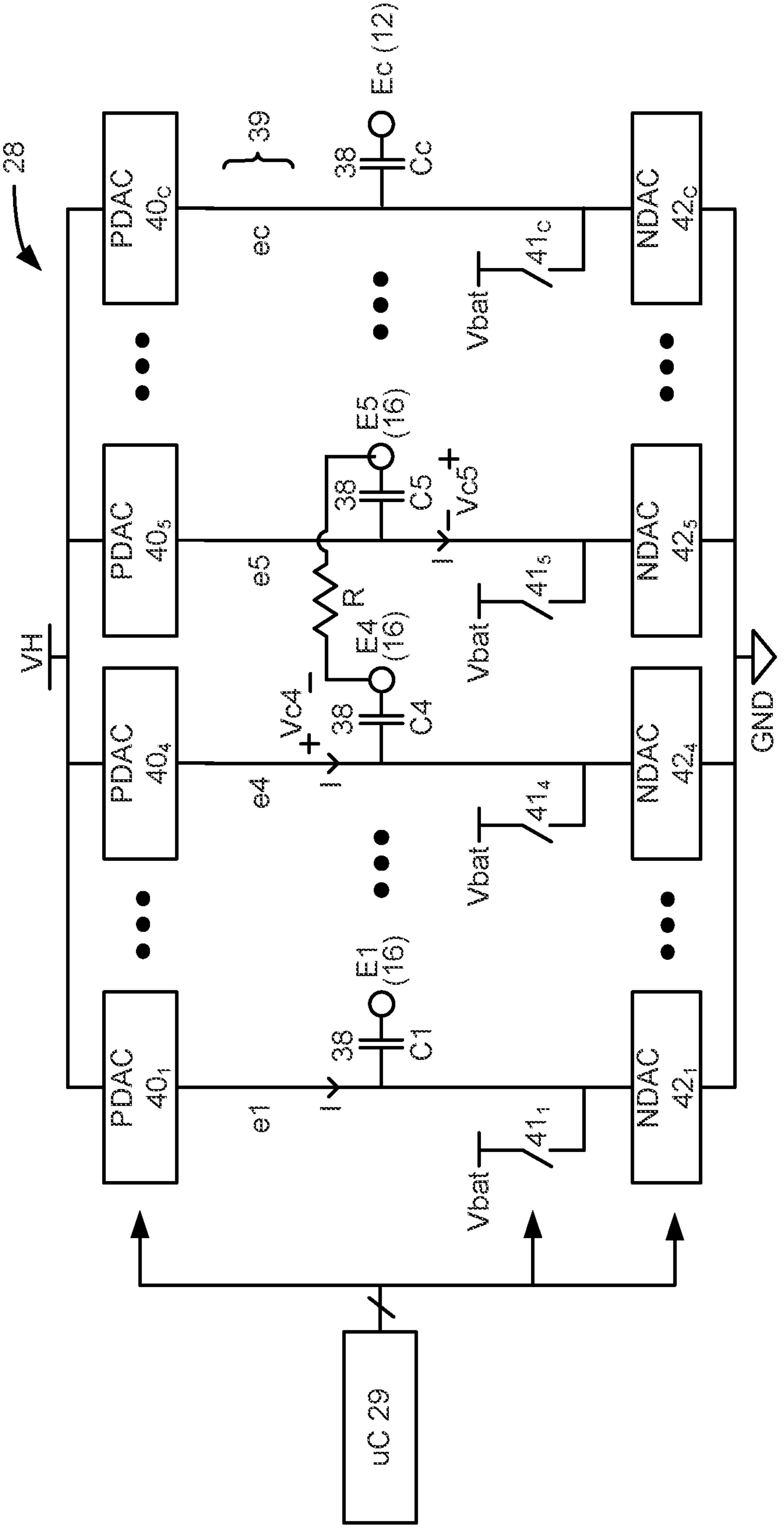
Figure 3 (prior art)
FIG. 3 shows stimulation circuitry used in the IPG to provide stimulation pulses, in accordance with the prior art.
Figure 4:
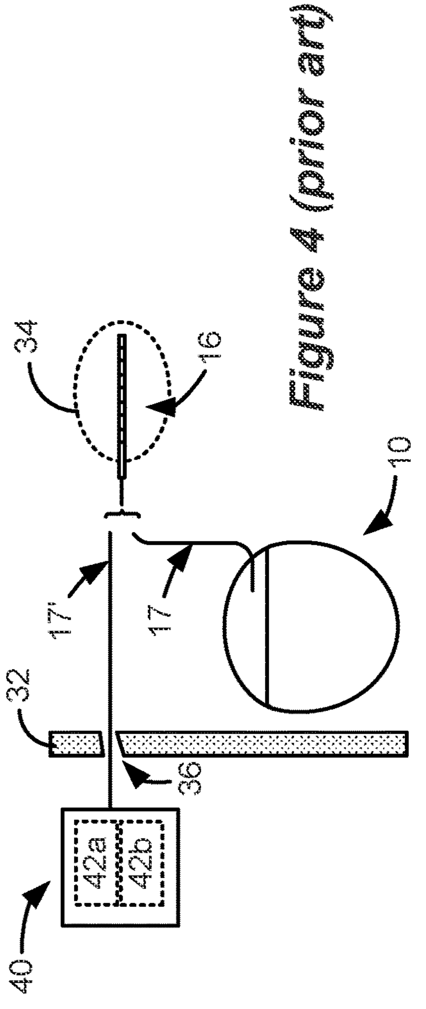
Figure 4 (prior art)
FIG. 4 shows an External Trial Stimulator (ETS) useable to provide stimulation before implantation of an IPG, in accordance with the prior art.
Figure 5:
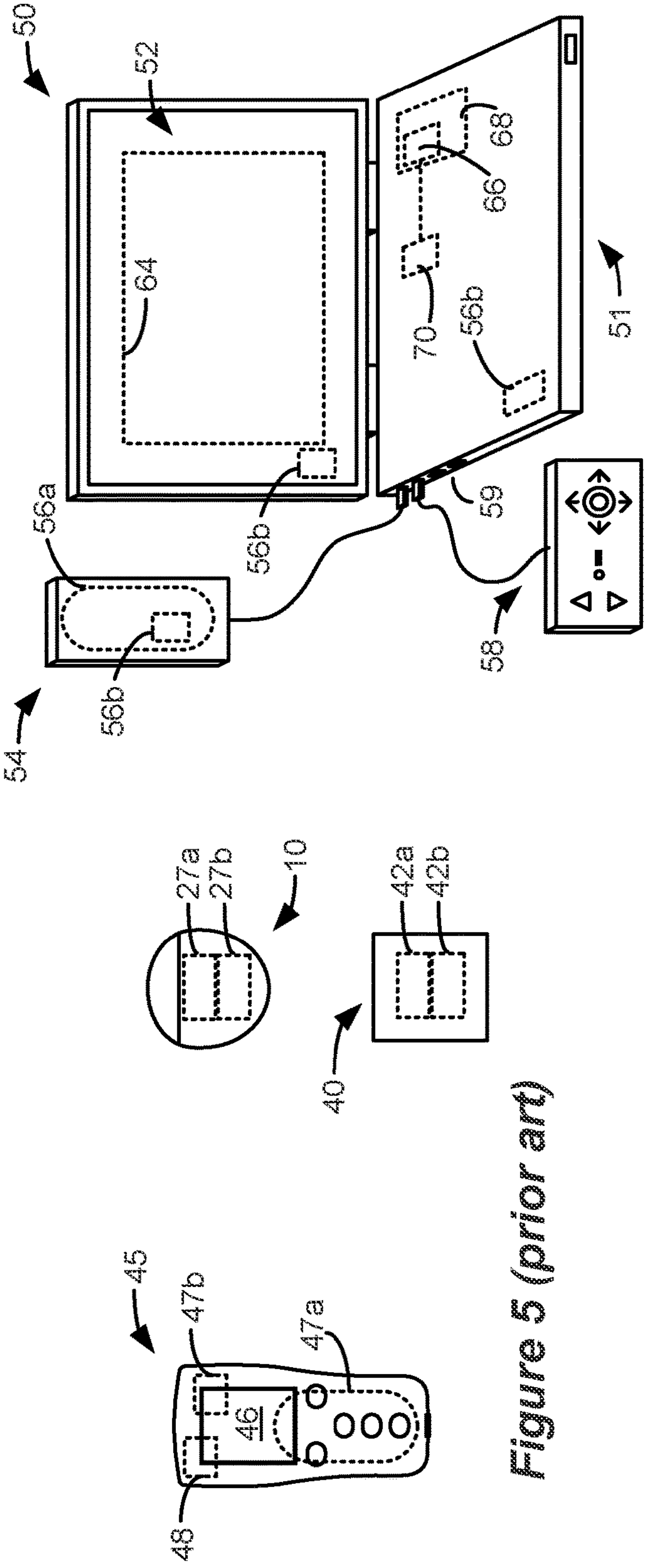
Figure 5 (prior art)
FIG. 5 shows various external devices capable of communicating with and programming stimulation in an IPG and ETS, in accordance with the prior art.
Figure 6:
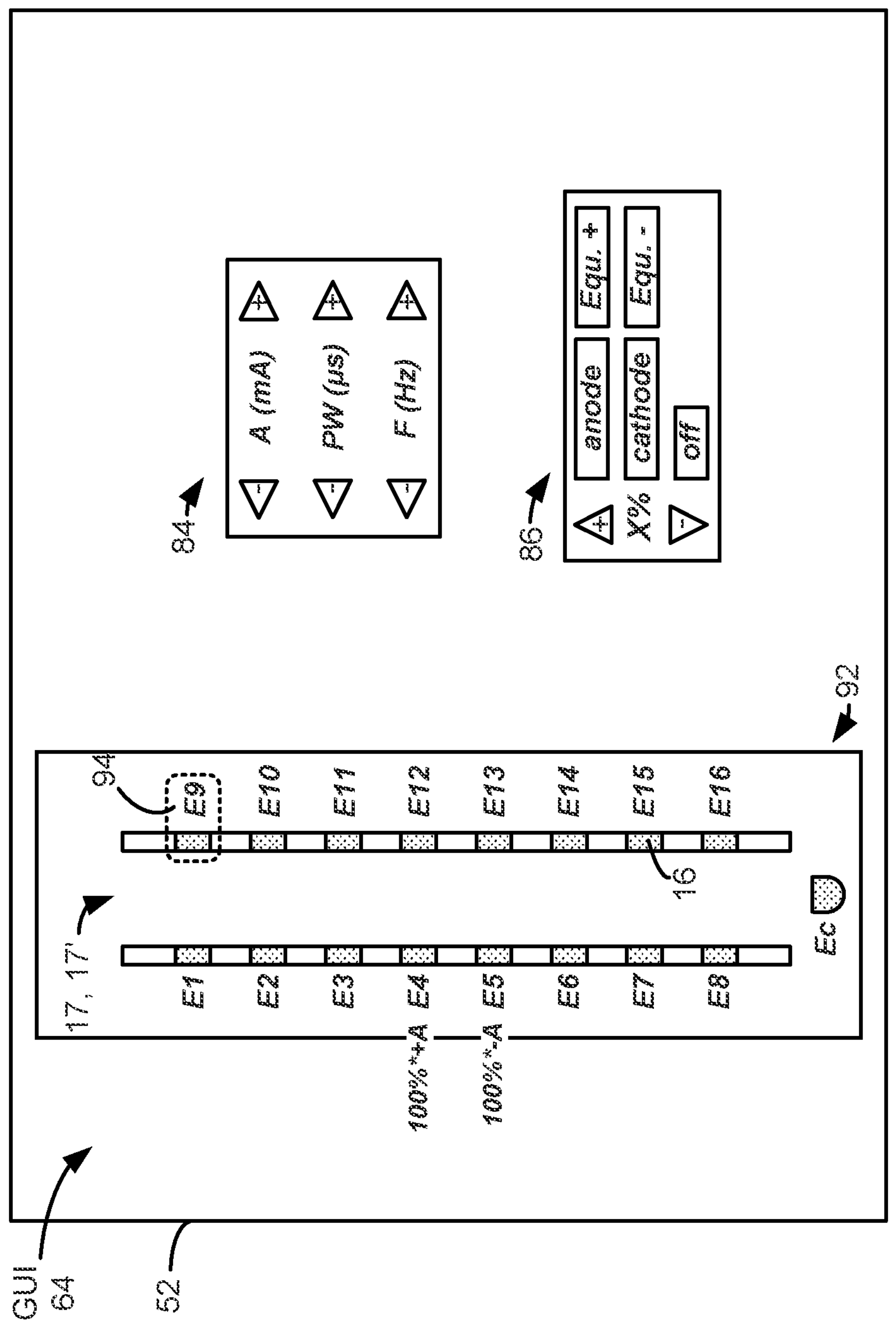
Figure 6 (prior art)
FIG. 6 shows a Graphical User Interface (GUI) of a clinician programmer external device for setting or adjusting stimulation parameters, in accordance with the prior art.

Aspects of this disclosure relate to systems and methods that provide and support the delivery of the patient's SCS therapy. One of the goals of such systems is to maintain and adjust the patient's therapy so as to provide effective pain relief and minimal side effects. Another goal may be to minimize energy usage (i.e., minimize battery drain). While SCS therapy can be an effective means of alleviating a patient's pain, such stimulation can also cause paresthesia. Paresthesia is a sensation such as tingling, prickling, heat, cold, etc. that can accompany SCS therapy. Generally, the effects of paresthesia are mild, or at least are not overly concerning to a patient. Moreover, paresthesia is generally a reasonable tradeoff for a patient whose chronic pain has now been brought under control by SCS therapy. Some patients even find paresthesia comfortable and soothing. SCS therapy that causes paresthesia may be referred to as supra-perception therapy. Nonetheless, at least for some patients, SCS therapy may ideally provide complete pain relief without paresthesia—what is often referred to as "sub-perception" or sub-threshold therapy, i.e., therapy that a patient cannot feel. U.S. Patent Publication No. 2021/0299448 ("the '448 Publication") and the priority applications cited therein describe methods and systems for providing sub-perception stimulation. The contents of the '448 Publication are hereby incorporated herein by reference. According to some embodiments, the sub-perception stimulation is configured to provide pain relief to the patient, wherein the pain relief washes in very quickly, for example, in less than an hour or less than ten minutes, or less than a minute, or less than ten seconds after beginning stimulation. The methods and systems described herein may be used with both supra- and sub-perception therapy.

When a patient is first implanted with spinal electrode leads, they will typically undergo a "fitting" process with their clinician, whereby the stimulation is calibrated to treat the individual patient's specific pain. The goal of the fitting process is to determine one or more stimulation programs that best treat the patient. As is known in the art, the stimulation programs may define parameters of the stimulation, such as frequency (v), amplitude (A) and pulse-width (PW), waveform shape, etc. Another aspect the fitting procedure is determining the best location along the lead for providing stimulation. By selecting which electrodes are active for supplying (or sinking) current, and how current is fractionated among those electrodes, the center-point of stimulation, as well as the focus of the resulting electric fields in the tissue, can be adjusted to best recruit neural elements in the spinal cord that are correlated to the location (i.e., the dermatome(s)) on the patient's body where the patient feels pain. This process is referred to as "sweet spot searching." Aspects of sweet spot searching are discussed in U.S. Patent Publication No. 2019/0366104, for example. As discussed in more detail below, the pulse width of the stimulation may also have an impact on the location of the patient's body where the patient will feel paresthesia. This is because the pulse width impacts which fibers are depolarized by the stimulation. For example, when other aspects of the stimulation are equal, increasing the stimulation pulse width tends to depolarize fibers that are deeper within the spinal cord. This can cause the location of paresthesia (i.e., the impacted dermatome) to shift caudally (downwardly on the patient's body).

Once the patient has undergone fitting, their IPG (of ETS) will be equipped with one or more stimulation programs that have been optimized for their pain. As mentioned above, the programs may specify the stimulation waveforms, pulse patterns, and parameters such as frequency (v), amplitude (A) and pulse-width (PW), etc. However, after the fitting process and during ongoing chronic therapy, the patient may wish to adjust the intensity of their therapy from time to time. Also, as explained further below, it may be beneficial to have periods of time when no stimulation is provided and/or when the stimulation is less than maximum intensity.

Figure 7:
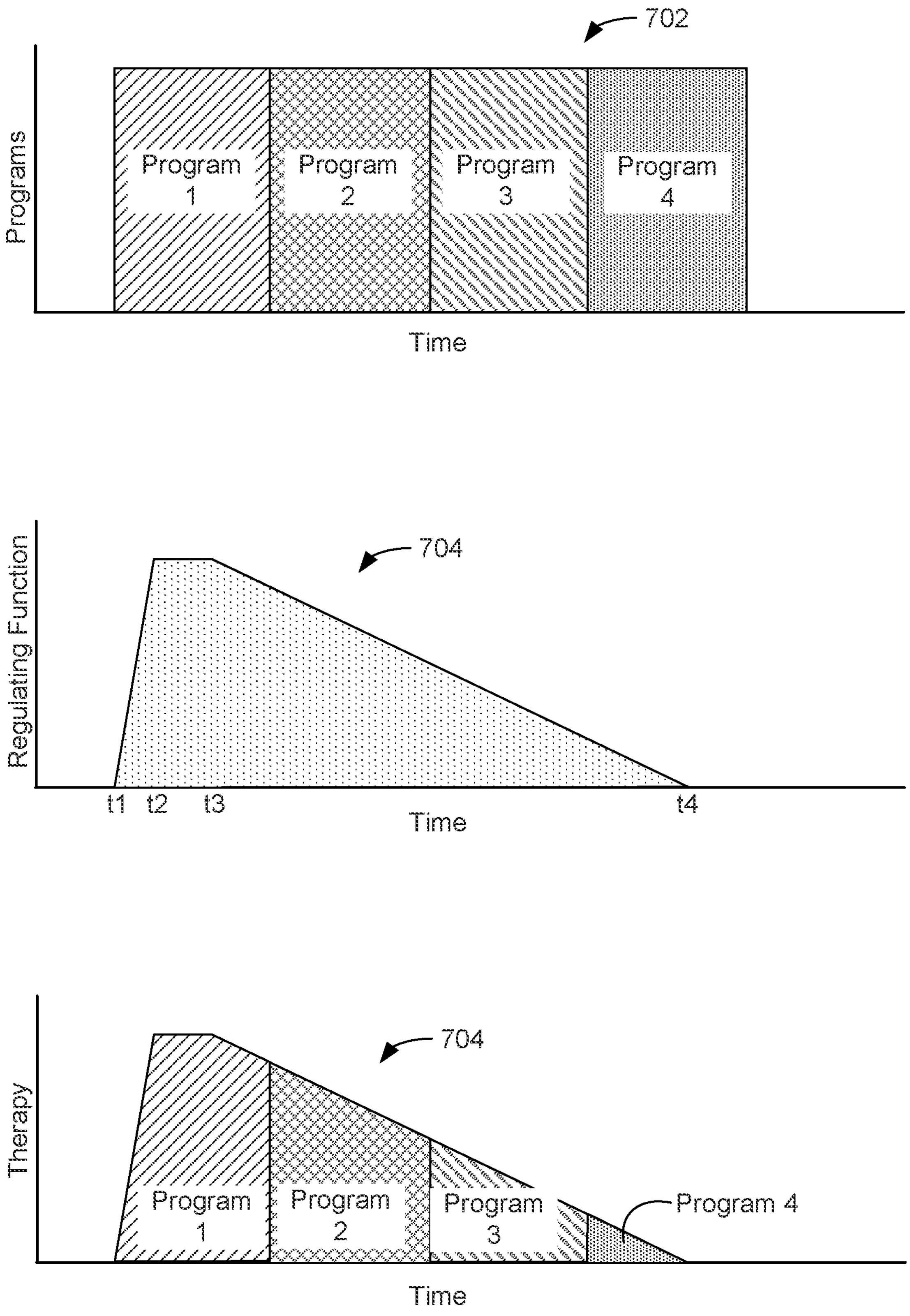
FIG. 7 shows an embodiment of using a regulating function to modulate stimulation intensity.

Accordingly, aspects of this disclosure relate to methods and systems for determining how to regulate the intensity of stimulation to achieve certain goals. For example, FIG. 7 illustrates a sequence 702 of four stimulation programs (programs 1-4). According to some embodiments, the clinician and/or the user may define schedule/order of the programs a priori. According to other embodiments, the user may select the schedule/order of the programs using their RC. According to some embodiments, the program sequence and scheduling may be informed based on data recorded using one or more internal or external sensors, as well as other input from the patient. Such sensor data and other input may be components of an integrated system for adaptively tailoring the patient's therapy, such as described in more detail below.

One aspect of adaptively regulating the patient's therapy may be to use a regulating/modulating function 704 that is combined (e.g., multiplied) with the stimulation program or sequence of programs to regulate/modulate the intensity of the stimulation, as a function of time. The illustrated regulating/modulating function 704 defines an intensity that ramps quickly over a first duration of t1 to t2, plateaus for a second duration of t2 to t3, and then ramps down over a third duration from t3 to t4. Of course, other regulating function shapes may be defined. For example, the regulating function could be a simple square wave, such that the stimulation is on for a certain duration of time and then is turned off for a second duration. The regulating function may be defined by the user and/or the clinician. As with the program schedule/order described above, the regulating function may be defined by the user and/or the clinician, and/or may be informed based on data recorded using one or more internal or external sensors, as well as other input from the patient.

The patient's therapy 706 at a given time is defined as a mathematical combination of the stimulation program running at that time and the regulating/modulating function. Specifically, the regulating/modulating function mathematically regulates the intensity of stimulation being delivered at a given time. For example, the stimulation program may be multiplied by the regulating/modulating function. Other mathematical combinations of the regulating function and the therapy program can be used, such as convolution, cross-correlation, and more complex time-variant operations in the space and/or time domain. U.S. Patent Publication No. 2020/0346019 describes methods and systems for modulating a stimulation program or sequence of programs using a modulating function.

Figure 8:
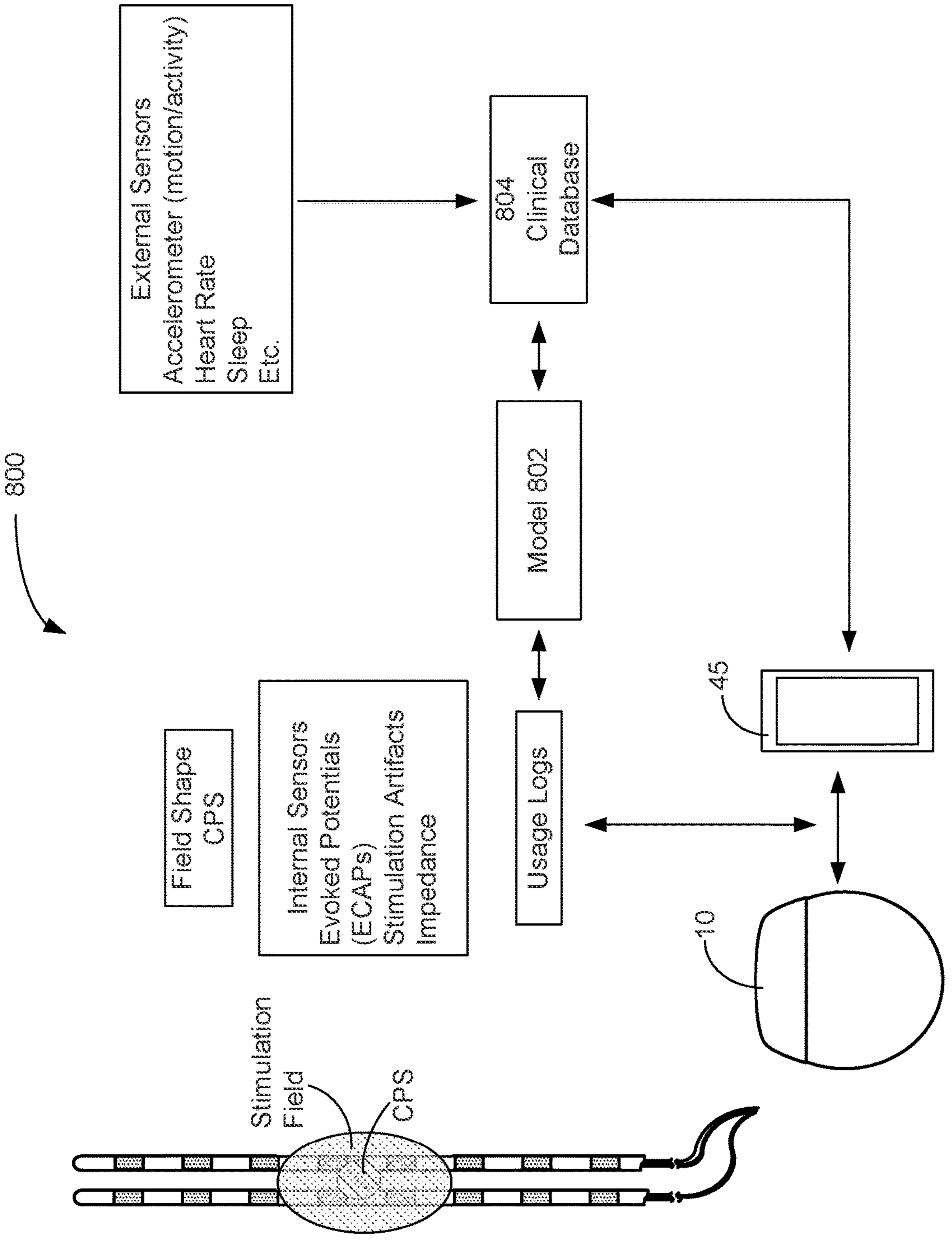
FIG. 8 shows an integrated system for managing aspects of a patient's SCS therapy.

FIG. 8 illustrates an embodiment of an integrated system 800 that includes aspects that may be used to derive or inform the scheduling, sequencing, and/or the regulating of the stimulation programs. The system may use various information to build a model 802 to inform how the patient's therapy can best be managed. The model may be built based (in part) on aspects of the patient's therapy that are related to, or measured by, the patient's IPG 10 and/or their RC 45 (which, as explained above, are in communication with each other). For example, the model may consider aspects of the geometry of the electric field (stimulation field), including the center-point of stimulation (CPS), that is created in the patient's tissue as a result of providing stimulation defined by the stimulation program(s). Information about the field geometry may typically be determined during the fitting process, as described above.

The model may also consider data recorded using the IPG 10. According to some embodiments, the IPG 10 may be configured to sense electrical signals that are present in the patient's tissue. See U.S. Patent Application Publication 2021/0236829 ("the '829 Application) for an example of an IPG comprising circuitry configured to sense such electrical signals. Some electrical signals may include neural signals such as Evoked Compound Action Potentials (ECAPs) that the stimulation evokes in the tissue. An ECAP comprises a cumulative response provided by neural fibers that are recruited by the stimulation, and essentially comprises the sum of the action potentials of recruited neural elements (ganglia or fibers) when they "fire." Various parameters relating to recorded ECAP signals can be determined, such as parameters relating to the amplitude, frequency, latency, etc. of the ECAP, as explained in the '829 Application. Another electrical signal that may be measured is the stimulation artifact, which comprises a voltage that is formed in the tissue as a result of the stimulation, i.e., as a result of the electric field that the stimulation creates in the tissue. Another electrical signal that may be measured is the electrical impedances that occur at the electrode/tissue interfaces.

The model may also consider usage logs, which may be provided from the patient's RC 45. The usage logs can provide analytics related to how the patient tends to adjust their therapy. For example, if the patient tends to repeatedly increase their stimulation at a certain point during the day, that may indicate that something characteristic about that time of day that triggers or exacerbates the patient's pain. Usage logs may also indicate which stimulation programs the patient like and dislikes. According to some embodiments, the patient may periodically use the RC to provide rankings of their pain and/or their therapy, for example, using questionnaires.

The system 800 may also include a clinical database 804, which may comprise a cloud-based data center/server. The clinical database 804 may be configured to exchange information with the patient RC 45, which may be internet connectable. The clinical database 804 may thereby receive RC- and IPG-related data from the RC. According to some embodiments, the model 802 (or aspects thereof) may be kept in the remote center/server. According to other embodiments, the model (or aspects thereof) may be resident in the patient's RC (or IPG).

The model 802 can also receive data from one or more external sensors as input. Examples of external sensors may include accelerometers (or other motion/activity sensors), heartrate monitors, sleep sensors, and the like. The model may use such data to correlate the patient's therapy to the patient's activity, for example.

One aspect of the patient's therapy that the model 802 may seek to control/adjust is the dosage and/or the intensity of the patient's therapy. The dosage may be expressed as the amount of charge Q (e.g., expressed in Coulombs) that a patient receives. The stimulation dose (i.e., the intensity) may be expressed as the charge per unit time, (e.g., charge per second (Q/s)). Embodiments of the disclosed methods and system concern determining appropriate dosages and durations for the stimulation provided to the patient.

Figure 9:
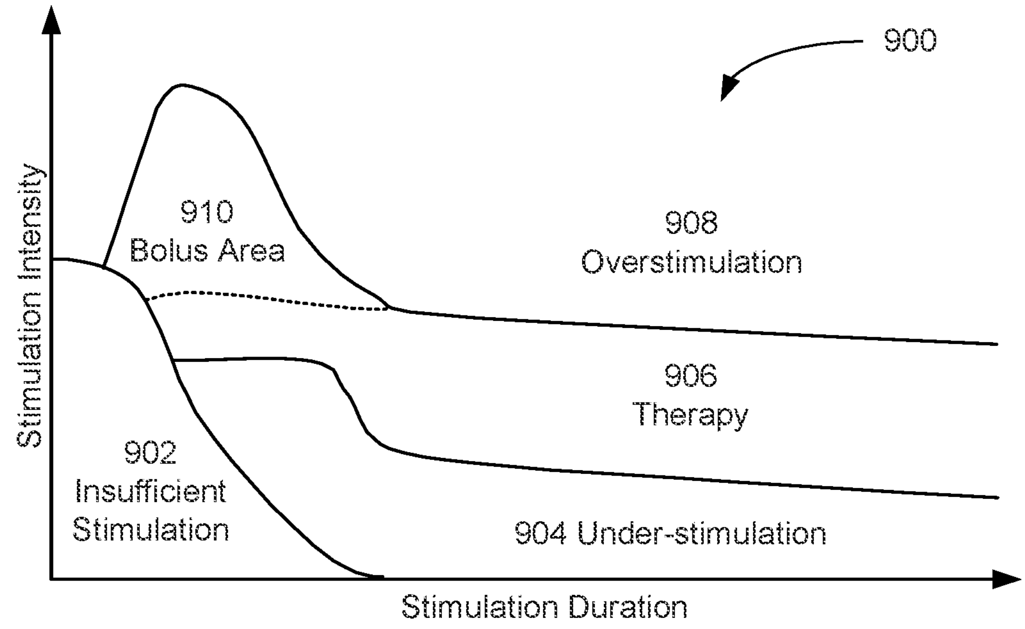
FIG. 9 shows qualitative relationships between stimulation intensity and stimulation duration.

FIG. 9 shows a graph 900 illustrating a qualitive relationship between stimulation intensity and stimulation duration. The graph 900 is divided into zones corresponding to different effects that certain combinations of intensity and duration may have on the patient. For example, if the duration of the stimulation is too short (zone 902), then even moderately intense therapy will fail to treat the patient's symptoms. Likewise, if the intensity of therapy is too low (zone 904), the therapy will be ineffective even if the duration is long. Effective therapy can be achieved when both the stimulation intensity and the stimulation duration are sufficient (zone 906). If the stimulation intensity is too high, then overstimulation can occur (zone 908). The stimulation may cause pain or other side effects for the patient.

Zone 910 is referred to as the bolus area. As used herein, "bolus stimulation" refers to a relatively high stimulation intensity applied for a relatively short duration (typically about 15-30 minutes), after which the stimulation is typically turned off for some length of time. The inventors have found that using one to several boluses of stimulation applied a few times throughout the day (e.g., 4-6 times) may treat the patients' pain even though stimulation is not applied continuously throughout that time.

Figure 10:
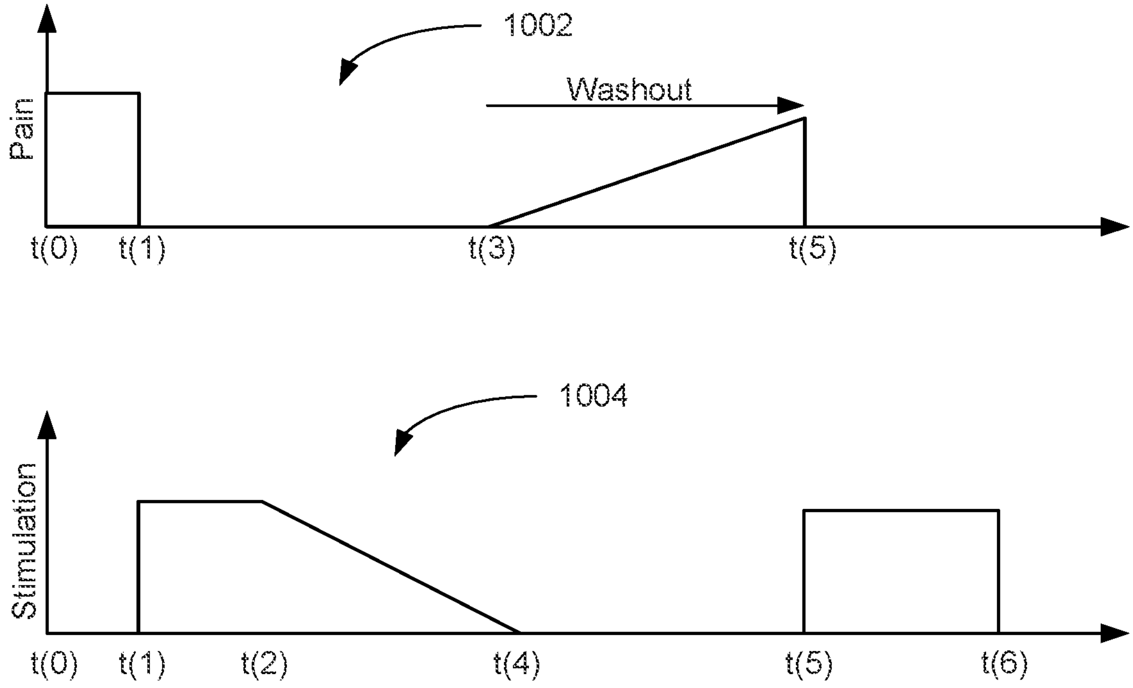
FIG. 10 illustrates a patient's pain response to stimulation cycling on and off.

FIG. 10 illustrates an example of how a patient's pain may respond to intermittent or bolus stimulation. Curve 1002 illustrates the patient's pain level and curve 1004 illustrates the therapy. Assume that at time t(0) the patient's pain is intense and the stimulation is off. At time t(1) the stimulation is applied, and the patient's pain level quickly drops (hopefully, to zero or close to zero). In other words, the therapy washes in very quickly. In the illustrated embodiment, the stimulation intensity is ramped down over a duration from t(2) to t(4). At some time as the stimulation is ramped down (or following the ramp down), the patient's pain begins returning. In the illustration, the patient's pain begins to return at time t(3). The process of the pain slowly returning once the stimulation is reduced or eliminated is referred to as "washout." In the illustration the therapy resumes at time t(5) and the patient's pain again drops very quickly.

Aspects of the disclosure relate to methods and systems for modulating the patient's therapy to account for washout. An aspect of this problem involves predicting the rate at which washout will occur, so that the stimulation can be managed to prevent the patient's pain from returning to a significant level. The inventors have found that the washout time depends on several factors, including (1) the stimulation duration; (2) the stimulation intensity; and (3) the passage of time since the patient first began receiving SCS therapy (for example, the time that has passed since the patient was first implanted with an IPG). Herein, the term "therapy history" is used to refer to the amount of time that has passed since the patient first began receiving SCS therapy. It is important to distinguish between the stimulation duration and the therapy history. The stimulation duration is the length of time that stimulation has been applied essentially without interruption. As used herein, stimulation duration is denoted as t-t(0), or Δt. The stimulation durations shown in FIG. 10 are the durations t(4)-t(1) and t(6)-t(5). The stimulation duration typically comprises multiple pulses of stimulation. The stimulation duration is typically at least a second, and may be many seconds, minutes, hours, days, weeks, or months. Likewise, the off time between the stimulation duration (i.e., the washout time) is also typically at least a second and may be seconds, minutes, hours, days, weeks, or months.

The stimulation duration should not be confused with the therapy history, which refers to the passage of time since the patient first began receiving SCS therapy. The therapy history is denoted herein as T−T(0), where T(0) is the time (or date) when the patient first began receiving SCS therapy. For example, T(0) may be on or near the day when the patient's IPG was implanted. Therapy history may also be denoted ΔT.

Figure 11:
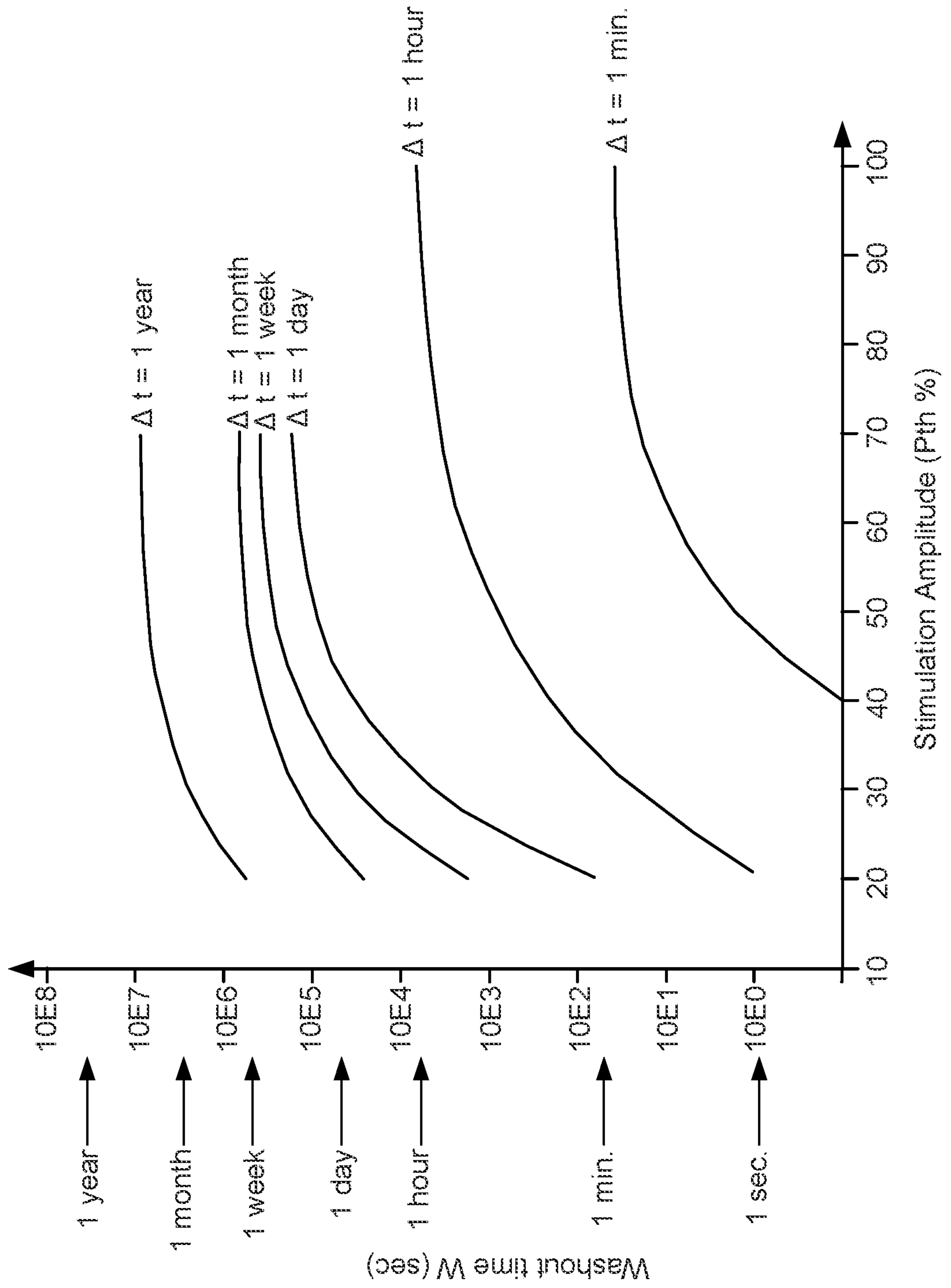
FIG. 11 illustrates relationships between washout rate and stimulation intensity.

FIG. 11 illustrates a graph relating washout time (W) on the y-axis as a function of stimulation intensity on the x-axis. Each of the separate plots correspond to different stimulation durations. The intensities are normalized with respect to patient's perception threshold (Pth). In other words, the intensity of 100% Pth is the intensity at which the patient can first perceive paresthesia arising from the stimulation. As mentioned above, the stimulation dose can be expressed as the charge per second (Q/s). The intensity is a product of the frequency (v), pulse width (PW), and amplitude (A) of the stimulation. In other words, (Q/s)=v(PW)A.

Generally, larger stimulation doses recruit more neural fibers, depolarize the fibers to a greater extent and/or for longer periods of time, and generate more action potentials. Also, generally, any of v, PW, and/or A can be manipulated to increase or decrease the stimulation dose Q/s. However, there are caveats. The electrical properties of the patient's biological tissue may impact the extent to which the frequency v may be adjusted while maintaining predictable behavior. Briefly, the patient's tissue can act as a low-pass filter since it comprises substantial amounts of water. Accordingly, different behavior and mechanisms of action may occur above frequencies of about 400-500 Hz. Thus, according to some embodiments, the frequency may be maintained below about 300 Hz. According to some embodiments, the stimulation frequency may be about 60 to about 90 Hz. Also, recall that the pulse width PW of the stimulation may be adjusted during the fitting process to preferentially target specific neural elements. Accordingly, the PW for the patient's stimulation program is typically defined during fitting and typically would not be manipulated for the purpose of adjusting the stimulation intensity for dosing (though it could, according to some embodiments). In other words, generally, the PW may be adjusted to modulate neural targeting and the stimulation amplitude may be adjusted to modulate dosing. All of this is to say that adjustments to the stimulation dose Q/s may most easily be accomplished by adjusting the stimulation amplitude (A) (though any one or more of the parameters could be adjusted).

Referring again to FIG. 11, notice that the washout time is a function of the stimulation amplitude. That is, higher stimulation intensities lead to longer washout times. Also, the washout time is a function of stimulation duration (Δt), with longer durations yielding longer washout times, even with relatively lower amplitude stimulation. Accordingly, both stimulation intensity and stimulation duration may be modulated to regulate the washout time.

Figure 12:
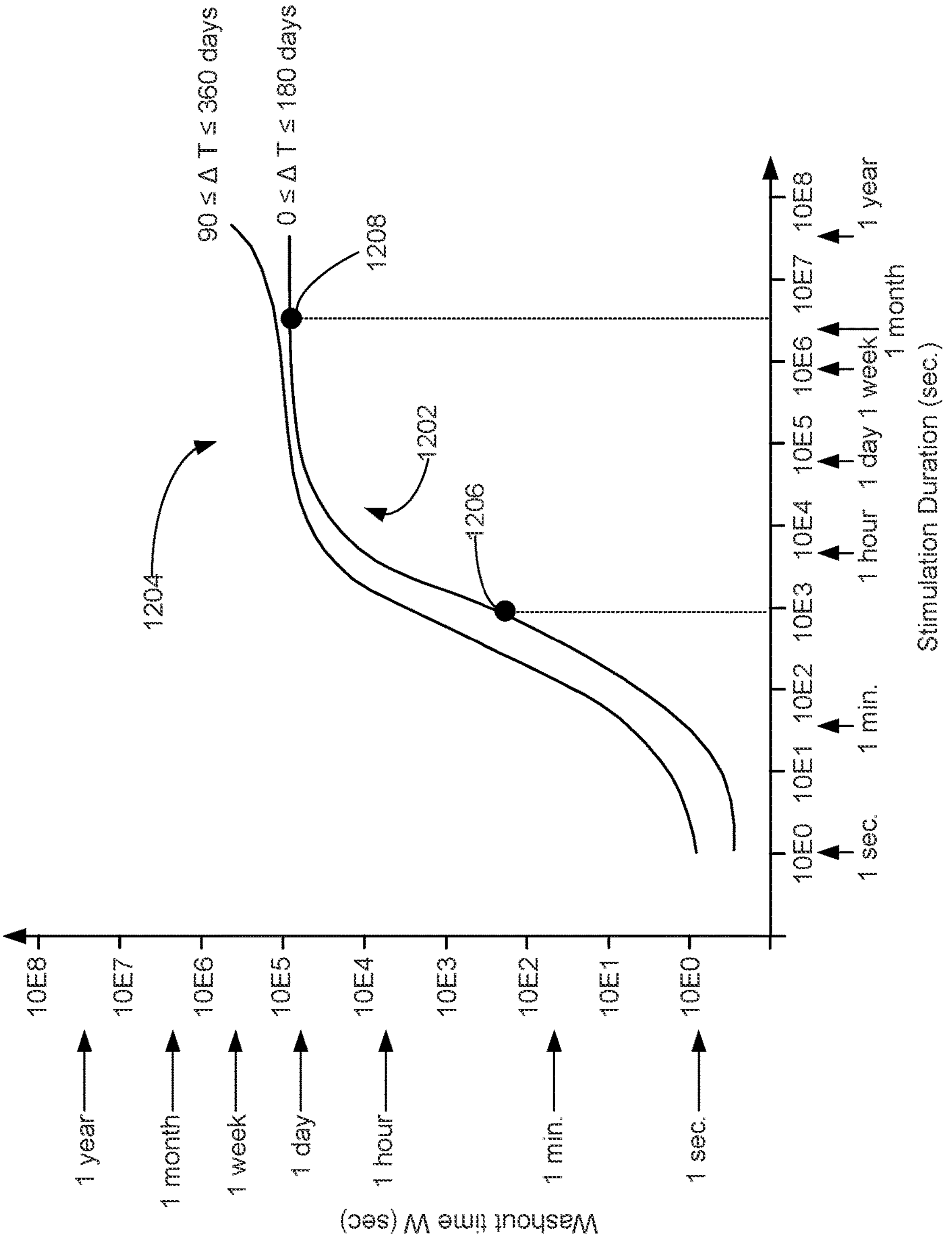
FIG. 12 shows relationships between washout rate and stimulation duration.

FIG. 12 shows a graph of washout time (W) on the y-axis as a function of stimulation duration (Δt) on the x-axis. Two curves are shown, each corresponding to different therapy histories (ΔT). The lowermost curve 1202 is for a therapy history that is between 0 and 180 days. In other words, the patient may have began receiving SCS therapy (for example, had their IPG implanted) sometime between 0 and 180 days prior to the collection of the data shown in the FIG. 12. The topmost curve 1204 has a therapy history that is between 90 and 360 days. Assume that all of the measurements were recorded using a stimulation that has an optimum stimulation dose Q(opt)/s. In other words, the stimulation uses an optimum pulse-width PW(opt) and an optimum stimulation amplitude I(opt). As mentioned above, the optimum PW(opt) may be determined for targeting the neural elements for blocking the patient's pain. The optimum stimulation amplitude A(opt) may be determined based on self-dosing (i.e., the amplitude that the patient chooses on their RC) and/or based on any of the measurements discussed above with reference to FIG. 8.

Notice that the washout time increases as a function of the stimulation duration (Δt). Also notice that the washout times are longer for longer therapy histories (ΔT). The inventors have discovered that, generally, the washout time W is proportional to the stimulation duration (Δt) multiplied by a coefficient a, which is a function of the stimulation dose (Q/s) and the therapy history (ΔT). That is: $W \propto \Delta t\ a(Q/s, \Delta T)$. The fact that the washout time is a function of the therapy history suggests that as the patient undergoes SCS therapy, some amount of neuroplasticity takes place in the patient's spine and/or in their brain. As a result, a patient with a longer therapy history needs less stimulation and/or stimulation less often than they did at earlier therapy history times to achieve the same washout times.

It will be appreciated that the curves 1202 and 1204 associate a first duration (i.e., the stimulation duration, during which stimulation is provided) with a second duration (i.e., the washout time). Information such as the information contained in the curves 1202 and 1204 may be used to determine aspects of a patient's stimulation therapy, such as determining a regulating function (e.g., function 704, FIG. 7). Since the curves indicate how washout time changes as a function of stimulation duration, they can inform how to cycle stimulation on and off so as to avoid washout (i.e., the return of the patient's pain) before stimulation is resumed. For example, according to some embodiments, the curves can be used to minimize stimulation duration (e.g., to save energy usage) while maximizing washout time. Accordingly, an aspect of the disclosed methods and systems comprises deriving curves (i.e., mathematical models) such as 1202/1204 for the patient, and selecting a stimulation duration using the curves.

Different locations on the curve can be used to inform the cycle times, depending on various operational goals. According to some embodiments, the stimulation duration (the time when stimulation is active) may be set at a value that corresponds to the maximum inclination of the curve (point 1206) (Note that the values discussed here are only shown on plot 1202. But similar values could be calculated for plot 1204, or whichever plot is appropriate for the patient's therapy history (ΔT)). The maximum inclination can be determined analytically as the point where the slope of the curve 1202 is at a maximum (that is, where the first derivative of the curve is maximum, the second derivative of the curve is 0, and the third derivative is less than 0). Selecting the stimulation duration at the point of maximum inclination of the curve provides the optimum efficiency for the stimulation, i.e., it maximizes the washout time with the minimum stimulation duration. According to some embodiments, if the on time for the stimulation is set for a stimulation duration corresponding to the maximum inclination, then the off time may be set at some fraction of the predicted washout time W(t), to allow a margin of safety. For example, the off time may be set at 75-80% W(t).

According to some embodiments, the stimulation duration may be set at the value on the curve corresponding to the minimum slope 1208. That duration would require longer duty cycles (perhaps days or weeks) and therefore increased energy usage. But such stimulation durations would provide less variability in washout times and might, therefore, be perceived as safer for the patient. According to some embodiments, if the stimulation duration is set for the minimal slope, then the off time may be set at or very near the time predicted by W(t). Generally, once a curve (such as 1202 or 1240) is determined for a patient, stimulation according to any predetermined point on the curve may be targeted, depending on the therapeutic goals.

Figure 13:
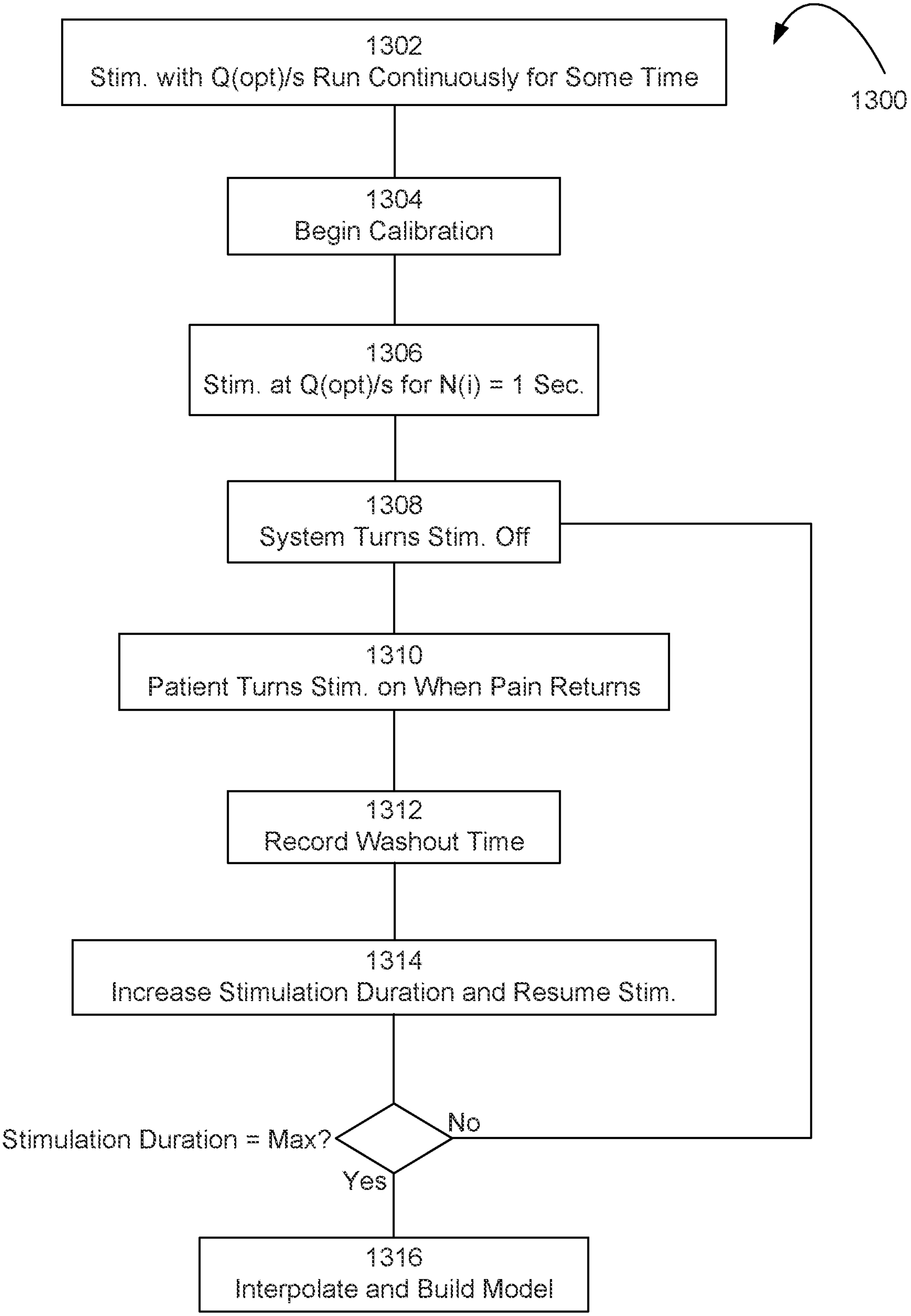
FIG. 13 shows an algorithm for determining washout time as a function of stimulation duration.

FIG. 13 illustrates and embodiment of an algorithm 1300 for determining a model of washout time as a function of the stimulation duration for a patient. At step 1302 assume that the patient has been using one or more stimulation programs continuously for some time. Assume that the patient is satisfied with the stimulation dose of the programs, denoted here as the optimum stimulation dose (Q(opt)/s). As described above, a clinician may have determined the optimum pulse width PW(opt) and frequency v during a fitting process, so as to target specific neural elements. The patient may be using an optimum stimulation amplitude A(opt) that they may have arrived at by adjusting the stimulation to a comfortable and effective level. The calibration routine begins at step 1304. When the calibration routine begins the optimum stimulation is continued for a first duration—1 second in this case (step 1306). At the end of the duration the system automatically turns off the stimulation (step 1308). According to some embodiments, the system may not inform the patient that the stimulation has ceased. According to some embodiments, the stimulation may only be turned off during the day when the patient is awake. The patient will begin to feel pain and turn their stimulation back on (step 1310) at some point. At step 1312 the system records the duration between when the stimulation was turned off and when the patient turned it back on (i.e., the washout time). At step 1314 the test stimulation duration is increased, and the steps 1308-1314 are repeated until the algorithm reaches a maximum stimulation duration to be tested. The stimulation duration may be increased in any manner. According to some embodiments, the stimulation duration is increases by doubling the previous stimulation duration (i.e., N=1, 2, 4, 8, 16, . . . ). The algorithm 1300 may test a range of stimulation durations up to a maximum stimulation duration. For example, the maximum stimulation may be about a week (about $10^6$ seconds). The algorithm interpolates the recorded stimulation durations and washout times and builds the model (step 1316) once the maximum stimulation duration to be tested is reached.

Note that other methods of determining a relationship between the washout time and the stimulation duration and/or the stimulation intensity may be used. For example, an algorithm could receive a desired washout time as input and then modulate different stimulation durations until the desired washout time is achieved. Alternatively, the algorithm may determine a relationship between stimulation intensity and washout time by modulating one of the values and interpolating its impact on the other. Note that the curves 1202 and 1204 shown in FIG. 12 depend on both the patient's therapy history and on the intensity of the stimulation. Accordingly, for a given therapy history the model may include multiple curves, each corresponding to different stimulation dose. The models may be embodied as curves, estimated functions, analytically derived functions, look-up tables, databases, and the like, which relate washout time (and, accordingly, a time at which the stimulation should be resumed) to the stimulation duration and/or the stimulation dose. The models may be resident in the patient's RC 45, IPG 10, or in a remote data site, such as the clinical database 804.

Figure 14:
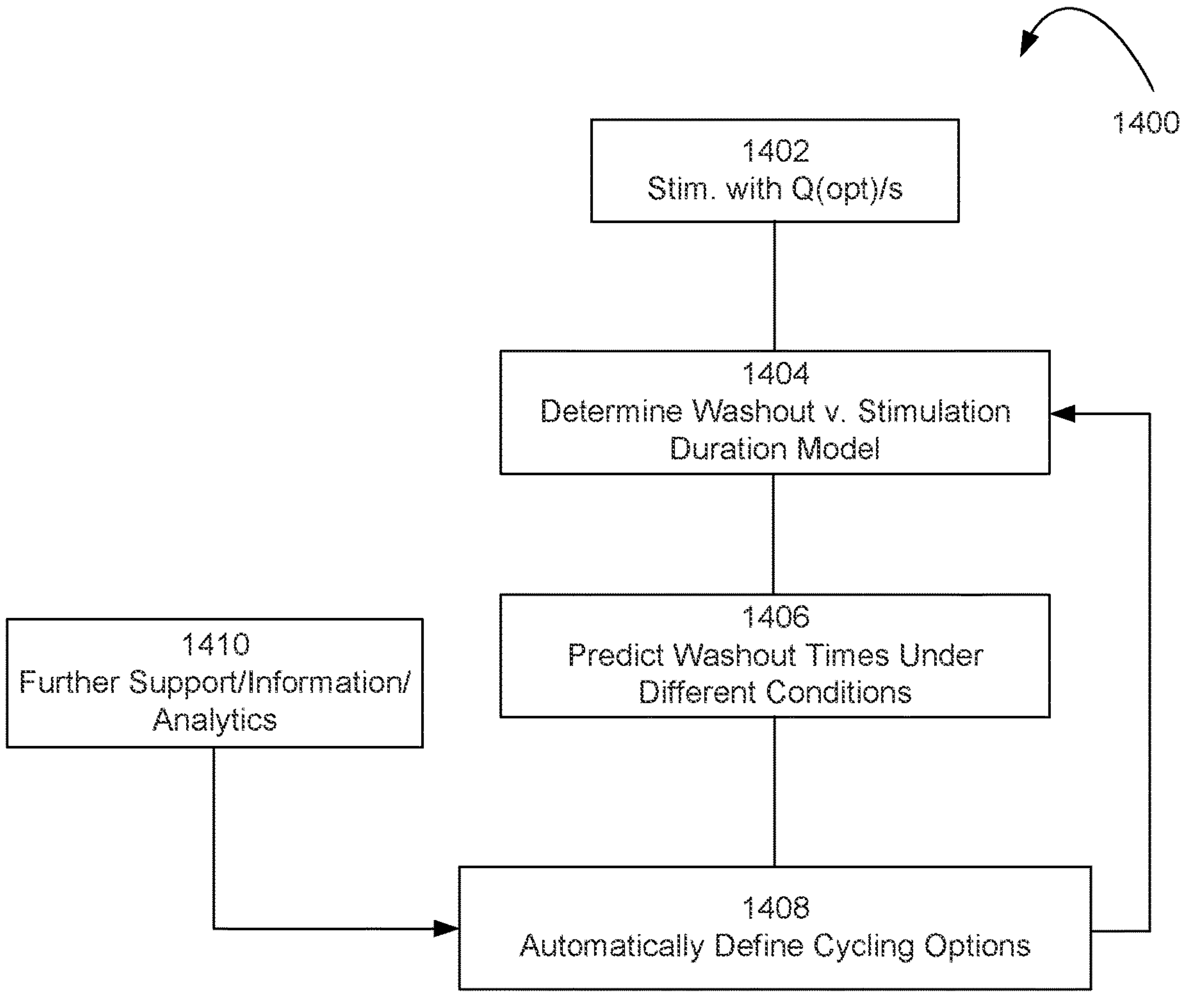
FIG. 14 shows an embodiment of an algorithm for determining stimulation cycling options based on predictions of washout times informed using a model of washout time as a function of stimulation duration.

FIG. 14 illustrates an embodiment of an algorithm 1400 for using the washout v. stimulation duration model. Assume that at step 1402 the patient is using an optimal therapy program on a continuous basis. At step 1404 the system can automatically characterize a washout v. stimulation duration model (and/or a washout v. stimulation intensity model), for example, using the algorithm 1300 (FIG. 13). Once derived, the model(s) can be used to predict washout times under different conditions (step 1406) and to automatically define cycling options (1408) for the patient's stimulation therapy. Specifically, the models can be used to define when the stimulation should be cycled on to avoid pain arising. For example, the model can be used to define a program sequence 702 and/or a regulating function (704) that modulates/adjusts the stimulation intensity and on/off time (see FIG. 7) to achieve therapeutic goals while optimizing energy consumption. According to some embodiments, in addition to providing an association between the stimulation duration and the washout time, the models can also use additional information and analytics to inform the scheduling/dosing. For example, in the context of a system such as the system 800 (FIG. 8), the model may use information from internal and/or external sensors. For example, when internal and/or external information suggests that the patient is active or otherwise likely to be more susceptible to pain upon washout, the algorithm may weight the stimulation duration more conservatively to prevent the therapy from washing out sooner than expected. For example, the algorithm may select a stimulation duration that is longer and/or that is located on the minimum slope part of the washout v. stimulation duration curve (see point 1208, FIG. 12), as discussed above. Alternatively, when the patient is less likely to be susceptible, the algorithm may configure the stimulation duration to coincide with the maximum inclination part of the washout v. stimulation duration curve (see point 1206, FIG. 12) to provide the most efficient use of energy. According to other embodiments, the algorithm may receive information related to an amount of charge remaining on the IPG's battery and may adjust cycling accordingly. According to some embodiments, the graphs, mathematical functions, look-up tables, databases, or the like, which associate the stimulation duration with an associated washout time may also be indexed according to the further information that the model may use to pick on/off times for cycling the patient's stimulation, such as information values derived from external sensors, internal measurements/recordings, therapy history, and/or stimulation intensity.

According to some embodiments, the stimulation may be cycled on and off based on the models and algorithms without input from the patient. According to some embodiments, the stimulation programs may provide sub-perception stimulation and the patient may not be aware that their stimulation is cycling on and off. According to other embodiments, the patient may select to cycle their stimulation on and off and/or select a stimulation duration. In such embodiments, the algorithms may determine when to automatically cycle the stimulation on based on the calculated washout time.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method of providing electrical stimulation to a patient's spinal cord to treat pain in the patient using one or more electrode leads implantable in the patient's spinal column, wherein each electrode lead comprises a plurality of electrodes, the method comprising:

providing a patient-specific model that models washout times as a function of stimulation durations, wherein the modeled washout times are indicative of a length of time it takes for the patient's pain to return once stimulation ceases, using the patient-specific model to determine an on-time during which stimulation is to be applied and a corresponding off-time during which stimulation is not to be applied, wherein the off-time is configured to be less than the modeled washout time for the corresponding on-time, and providing stimulation to the patient according to the determined on- and off-times.

2. The method of claim 1, wherein the electrical stimulation is configured to be below the patient's perception threshold and to provide pain relief to the patient.

3. The method of claim 2, wherein the electrical stimulation is configured so that the pain relief washes in in a period of ten seconds or less.

4. The method of claim 1, wherein determining the on and off times further comprises using one or more stimulation parameters to select the on and off times.

5. The method of claim 4, wherein the one or more stimulation parameters comprise one or more of stimulation intensity, stimulation amplitude, and/or stimulation dose.

6. The method of claim 1, wherein determining the on and off times further comprises using one or more parameters determined using one or more sensors selected from the group consisting of accelerometers, motion detectors, heart rate monitors, sleep sensors.

7. The method of claim 1, wherein determining the on and off times further comprises using one or more features of electrical signals recorded at one or more of the electrodes.

8. The method of claim 1, further comprising deriving the model by:

(a) providing test stimulation to the patient for a test first duration, (b) turning off the test stimulation at the end of the test first duration, (c) after a test second duration following the turning off the test stimulation, receiving an indication that the patient has turned on the stimulation, (d) increasing the length of the test first duration, (e) repeating steps (a)-(d) a plurality of times to collect a plurality test first durations and test second durations, and (f) modeling a relationship between test first durations and test second durations.

9. A system for providing electrical stimulation to a patient's spinal cord to treat pain in the patient using one or more electrode leads implantable in the patient's spinal column, wherein each electrode lead comprises a plurality of electrodes, the system comprising:

a memory programmed with a patient-specific model that models washout times as a function of stimulation durations, wherein the modeled washout times are indicative of a length of time it takes for the patient's pain to return once stimulation ceases, and control circuitry configured to use the patient-specific model to determine an on-time during which stimulation is to be applied and a corresponding off-time during which stimulation is not to be applied, wherein the off-time is configured to be less than the modeled washout time for the corresponding on-time, and to provide stimulation to the patient according to the determined on- and off-times.

10. The system of claim 9, wherein the electrical stimulation is configured to be below the patient's perception threshold and to provide pain relief to the patient.

11. The system of claim 10, wherein the electrical stimulation is configured so that the pain relief washes in in a period of ten seconds or less.

12. The system of claim 9, wherein determining the on and off times further comprises using one or more stimulation parameters to select the on and off times.

13. The system of claim 12, wherein the one or more stimulation parameters comprise one or more of stimulation intensity, stimulation amplitude, and/or stimulation dose.

14. The system of claim 9, wherein determining the on and off times further comprises using one or more parameters determined using one or more sensors selected from the group consisting of accelerometers, motion detectors, heart rate monitors, sleep sensors.

15. The system of claim 9, wherein determining the on and off times further comprises using one or more features of electrical signals recorded at one or more of the electrodes.

16. The system of claim 9, wherein the control circuitry is further configured to derive the model by:

(a) providing test stimulation to the patient for a test first duration, (b) turning off the test stimulation at the end of the test first duration, (c) after a test second duration following the turning off the test stimulation, receiving an indication that the patient has turned on the stimulation, (d) increasing the length of the test first duration, (e) repeating steps (a)-(d) a plurality of times to collect a plurality test first durations and test second durations, and (f) modeling a relationship between test first durations and test second durations.

* * * * *